United States Patent [19]

Hsu

[11] Patent Number: 5,576,217

[45] Date of Patent: Nov. 19, 1996

[54] SOLID PHASE MICROEXTRACTION OF TRACE AMOUNTS OF ORGANIC ANALYTES

[75] Inventor: C-P. Sherman Hsu, Basking Ridge, N.J.

[73] Assignee: Mallinckrodt Baker, Inc., Phillipsburg, N.J.

[21] Appl. No.: 396,124

[22] Filed: Feb. 28, 1995

[51] Int. Cl.$^6$ ..................................... G01N 30/48
[52] U.S. Cl. .......................... 436/126; 436/139; 436/140; 436/103
[58] Field of Search .................................. 436/124, 126, 436/103, 178, 139–140

[56] References Cited

FOREIGN PATENT DOCUMENTS

WO91/15745  10/1991  WIPO ............................. G01N 1/02

OTHER PUBLICATIONS

Water Pollution Mesearch Journal of Canada, vol. 24, No. 1, pp. 179–191 (1989).

Analytical Chemistry, vol. 62, No. 19, pp. 2145–2148 (1990).

Analytical Chemistry, vol. 59, No. 10, pp. 1475–1478 (1987).

A. A. Boyd–Boland et al., Environ. Sci. Technol. vol. 28, No. 13, pp. 569A–574A (1994).

Z. Zhang et al., Analytical Chemistry, vol. 66, No. 17, pp. 844A–853A (Sep. 1, 1994).

R. Shirey et al. "Analysis of Environmental Samples Using Solid Phase MicroExtraction (SPME)", Pittsburg Conference, 20 pp, Mar. 1994.

*Primary Examiner*—Lyle A. Alexander
*Attorney, Agent, or Firm*—Parmelee, Bollinger & Bramblett; George W. Rauchfuss, Jr.

[57] ABSTRACT

A method for enhancing detection sensitivity of suspected trace amounts of organic analytes and particularly semivolatile organic analytes extractable from a sample by an organic solvent carrier matrix and subsequent extraction and analysis of said trace organic analytes by SPME wherein the improvement comprises exchanging the organic solvent carrier matrix containing the trace organic analytes for an aqueous carrier matrix before performing SPME fiber extraction and detection of the trace organic analytes.

20 Claims, 9 Drawing Sheets

SOLID PHASE MICROEXTRACTION OF TRACE AMOUNTS OF ORGANIC ANALYTES

FIELD OF THE INVENTION

The invention relates to an improved method for detecting trace amounts of organic analytes, particularly semivolatile organic analytes, and achieving better detection sensitivity with respect thereof. The invention more specifically relates to an improved solid phase microextraction process using a fiber for detecting trace amount of semivolatile organic analytes, such as for example pesticide residues in environmental samples, and achieving better detection sensitivity with respect thereof.

BACKGROUND OF THE INVENTION

Generally in analysis of samples, such as in analysis of environmental samples such as soil, water, fly ash, tissue or other materials, for trace residues of analytes of interest from matrices it is common to extract and then enrich or concentrate the content of the analytes in order to achieve better detection sensitivity. Among the enrichment methods commonly used there may be mentioned, for example, simple concentration of a dilute solution containing organic analytes by reducing the content of the solvents; liquid-liquid or liquid-solid (solid phase) extraction, generally followed by concentration of the extracts; gas-solid extraction or purge and trap methods, generally followed by desorption of analytes from solids or traps; leeching/extracting of analytes from solid samples with an organic solvent using techniques such as those employing a SOXHLET apparatus; and supercritical fluid extractions.

However, the use of organic solvents present problems of disposability, toxicity and the like. Therefore, recently a solid phase microextraction (SPME) process was developed by Janusz Pawliszyn of the University of Waterloo, Ontario, Canada, to eliminate solvent usage. The SPME process and apparatus therefor is disclosed for example in International Patent (PCT) Publication WO 91/15745 of J. Pawliszyn, published Oct. 17, 1991, and incorporated herein by reference thereto.

In said SPME process, a coated or uncoated fiber housed within a needle of a syringe is brought into contact with components/analytes in a fluid carrier or headspace above the carrier for a sufficient period of time for extraction of the analytes to occur onto the fiber or coated fiber. Subsequently the fiber is removed from the carrier or headspace above the carrier and the analytes desorbed from the fiber generally by thermal desorption into an analytical instrument, such as a gas chromatograph (GC), for detection and quantification of the analytes.

SPME has been shown to be a very useful sample preparation technique for a variety of analytes. However, SPME extraction and detection has some very serious limitations. One particularly serious limitation is in relation to attempting to utilize SPME for extractions of trace organic analytes in organic solvent carrier matrices. Basically, SPME generally cannot be applied to extraction of trace amounts of organic analytes from organic solvent carrier matrices, such as hexane. Attempts to apply SPME to extraction of trace amounts of organic analytes from organic solvents carrier matrices do not provide acceptable results because the solvent matrix is extracted by the coated fiber of the SPME device. SPME fibers for extraction of organic analytes are generally coated with an organic phase, such as the non-polar poly(dimethylsiloxane) (PDMS). Instead of the trace organic analytes being adsorbed on or into the organic phase coating on the fiber, the solvent carrier matrix components are themselves adsorbed or extracted onto the organic phase due to their overwhelmingly predominant presence in the sample. This prevents selective, efficient extraction of the trace organic analytes. For this reason SPME has not found any practical applicability for extraction of trace organic analytes from organic solvent carrier matrices. Rather, SPME carrier matrices have generally comprised predominantly aqueous matrices, for example water, a water-methanol (95:5) matrix or an aqueous inorganic salt solution matrix.

This is a particularly serious limitation on the use of SPME extraction procedure since many common sample enrichment and preparation techniques for organic analysis and detection of trace amounts of organic analytes in a sample involve contacting the sample with an organic solvent carrier matrix to dissolve the organic analytes in the organic solvent carrier matrix, or in some way extracting the trace organic analytes into an organic solvent carrier matrix. For example, United States Environmental Protection Agency (EPA) Methods 608 and 525.1 require liquid-liquid extraction or liquid-solid extraction of semivolatile organic compounds, such as pesticides and polyaromatic organic compounds, from aqueous samples, such as municipal and industrial discharges or drinking water, into organic solvents. Organic solvents are used because the organic solvents have a high dissolution capability/power for the organic analytes. Subsequent concentration of the extracts and analysis thereof can give reasonable good detection. However, detection sensitivity is not particularly good and generally detection of trace amounts of less than 1 ppb are difficult or impossible to obtain with a mass spectrometer. Moreover, attempts to apply SPME methodology to this type of analysis for trace organic analytes in an organic solvent carrier matrix have failed to give selective extraction of the trace organic analytes out of the organic solvent carrier matrix due to the overwhelmingly predominant presence of said organic solvent carrier matrix as mentioned hereinbefore.

SUMMARY OF THE INVENTION

Accordingly, it is an object of this invention to provide a methodology to enable SPME extraction and detection procedures to be applied to trace organic analytes extracted or dissolved in an organic solvent carrier matrix. A further object of the invention whis to provide a methodology to enable SPME extraction and detection procedures to be applied to trace amounts of semivolatile organic analytes extracted or dissolved in an organic solvent carrier matrix. A still further object of this invention is to provide a SPME procedure for detection of trace organic analytes, and particularly trace semivolatile organic analytes extracted or dissolved into an organic solvent carrier matrix, that achieves significantly enhanced detection sensitivity, i.e. a 100-fold or more increased detection sensitivity. A still further additional object of this invention is to provide a SPME procedure for detection of trace organic analytes, and particularly semivolatile organic analytes which are extracted or dissolved in organic solvent carrier matrices. A still further additional object of this invention is to provide a detection methodology for detection of such trace organic analytes to a detection sensitivity level which is presently very difficult or nearly impossible to reach with existing techniques and instrumentation, i.e. to detection levels of parts per quadrillion (ppq).

According to the invention a method has been developed to make the use of SPME procedures useful for extraction and detection of trace organic analytes from an organic solvent carrier matrix. The invention comprises taking a step against conventional wisdom, knowledge and practice in that the improvement comprises a carrier matrix exchange step to convert a highly unfavorable condition for SPME fiber extraction of trace organic analytes to a highly favorable condition. According to the invention, aqueous carrier matrix is exchanged for an organic solvent carrier matrix. Such an exchange goes against conventional wisdom because many organic analytes are considered to be insoluble in water. However, in this invention it has been discovered that replacement of the organic solvent carrier matrix for trace organic analytes with an aqueous carrier matrix results in homogenous aqueous solutions of the water and the trace organic analytes providing a highly favorable environment or condition for use of SPME in trace organic analysis. Apparently, organic compounds considered insoluble in water are soluble in aqueous matrices at trace or ultratrace levels such as ppm, ppb, ppt and ppq.

The invention therefore comprises a method for enhancing detection sensitivity of suspected trace amounts of organic analytes and particularly semivolatile organic analytes dissolved in an organic solvent carrier matrix or extractable from a sample by an organic solvent carrier matrix and subsequent extraction and analysis of said trace organic analytes by SPME wherein the improvement comprises exchanging the organic solvent carrier matrix containing the trace organic analytes for an aqueous carrier matrix before performing SPME fiber extraction and detection of the trace organic analytes.

The improved method of this invention for the detection of trace amounts of organic analytes from environmental sample comprises:

(1) providing an environmental sample suspected of containing trace amounts of organic analytes, (2) if said environmental sample does not already have an organic solvent carrier matrix, organic solvent-extracting any such trace amounts of organic analytes from said environmental sample into an organic solvent carrier matrix in which said trace amounts of organic analytes are soluble, (3) optionally concentrating said trace amounts of organic analytes in said organic solvent carrier matrix by removal of a portion of said organic solvent, (4) thereafter, exchanging said organic solvent carrier matrix by the addition thereto of water to form a mixture and removing said organic solvent carrier matrix therefrom producing a detection sample comprising an aqueous carrier matrix containing said trace amounts of organic analytes, and thereafter performing SPME on said detection sample by (5) placing a fiber of a SPME extraction device in contact with said aqueous carrier matrix or a confined headspace above said aqueous carrier matrix for a sufficient period of time for extraction of the trace organic analytes from the aqueous carrier matrix and onto the fiber to occur, (6) subsequently removing said fiber from said aqueous carrier matrix or confined headspace and desorbing the organic analytes from the fiber into an analytical instrument for detection of one or more of said trace organic analytes, and (7) detecting one or more of said organic analytes in said analytical instrument.

BRIEF DESCRIPTION OF THE DRAWINGS

The invention is illustrated in connection with the following drawings in which.

DETAILED DESCRIPTION OF THE INVENTION

The improved detection procedure of this invention can be utilized to detect a broad range of trace organic analytes using a non-selective fiber coating or a selective sample of organic analytes using a selective fiber coating. The improved procedure can be utilized with any organic solvent carrier dissolved or extracted sample from any environment, such as outdoor in nature or in industrial process streams or the like. Thus, the term environmental sample is meant to include a trace organic compound-containing sample from any environment.

The SPME device for carrying out the improved process of this invention is described in the aforementioned PCT Publication WO 91/15745 the disclosure of which has been incorporated herein by reference thereto. Such a SPME device is available from Supelco Inc. of Bellefonte, Pa., and need not be described further.

The improved procedure of this invention is particularly useful in detection of trace or ultratrace amounts of semivolatile organic analytes such as pesticides, herbicides, polychlorinated biphenyl compounds and polynuclear aromatic hydrocarbon compounds, especially at ppb, ppt and ppq levels.

The matrix exchange, whereby (1) a suitable amount of water is added to organic solvent carrier matrix of the test sample containing the trace organic analytes and (2) the organic solvent carrier matrix is removed to provide the aqueous carrier matrix based detection sample, can be accomplished by any suitable means of removing the solvent, generally by evaporation of the organic solvent carrier utilizing a rotary evaporator or a Kuderna-Danish evaporator or the like or by membrane separation or the like.

Once the organic solvent carrier matrix has been replaced by an aqueous carrier matrix, a typical SPME extraction and detection procedure can be conducted on the aqueous carrier matrix based detection sample containing trace organic analytes. After extraction of the trace organic analytes on the SPME device fiber, the trace organic analytes are desorbed from the fiber in a suitable high resolution instrument such as a gas chromatograph (GC) with a mass spectrophotometer (MS), an electron capture detector (ECD) or a flame ionization detector (FID) or the like. Desorption can be accomplished by any suitable method, usually by direct heating, laser desorption, or conductive heating, for example microwave desorption or by the Curie point magnetic hysteresis method.

This invention is particularly useful for the detection of trace and ultratrace amount of semivolatile organic analytes, i.e. organic analytes having a boiling point at least about 25° C. higher, preferably about 50° C. or more higher than the organic solvent carrier matrix into which they have been extracted from the environmental sample.

The time the fiber is contacted with the aqueous matrix or a confined headspace above the aqueous matrix will vary but will generally range from about 1 minute to 30 minutes or more depending on the analytes being detected, the system and the device employed.

Direct SPME of trace organic analytes from extraction solutions in which the analytes are dissolved in solution carrier matrices that are predominantly or completely organic solvents is demonstrated to result in poor, unsatisfactory results due to the overwhelming presence of the organic solvent carrier preventing extraction of the trace organic analytes by the following example.

COMPARATIVE EXAMPLE 1

A SPME silica fiber of a Supelco SPME device, which fiber is coated with 7 μm of poly(dimethylsiloxane), was inserted for seven minutes into a test sample solution containing 1 ppb of each of the following eighteen pesticides in 1 ml hexane carrier matrix.

| | |
|---|---|
| Aldrin | Endosulfan I |
| α-BHC | Endosulfan II |
| β-BHC | Endosulfan sulfate |
| γ-BHC | Endrin |
| δ-BHC | Endrin aldehyde |
| 4,4'-DDD | Endrin ketone |
| 4,4'-DDE | Heptachlor |
| 4,4'-DDT | Heptachlor epoxide |
| Dieldrin | Methoxychlor |

Figure 1:
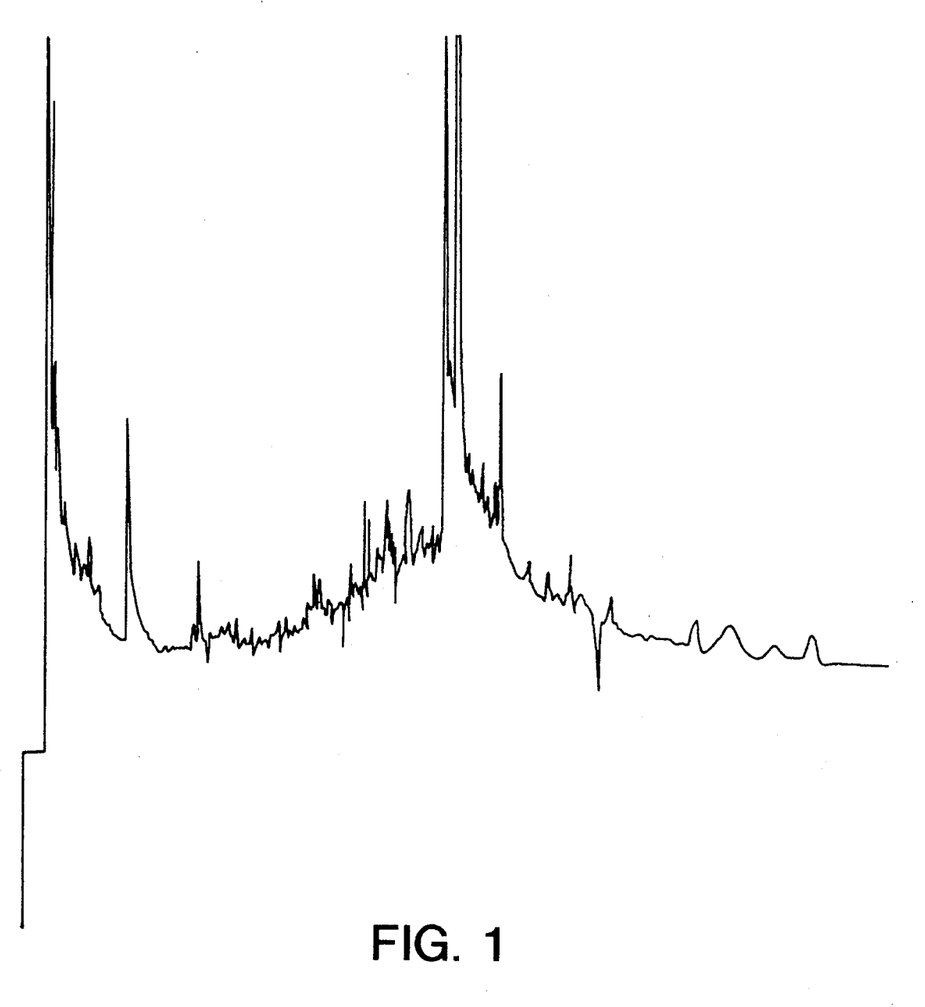
FIG. 1 is a chromatogram of an attempt to detect trace organic pesticide analytes in an organic solvent (hexane) carrier matrix by SPME methodology.
Figure 2:
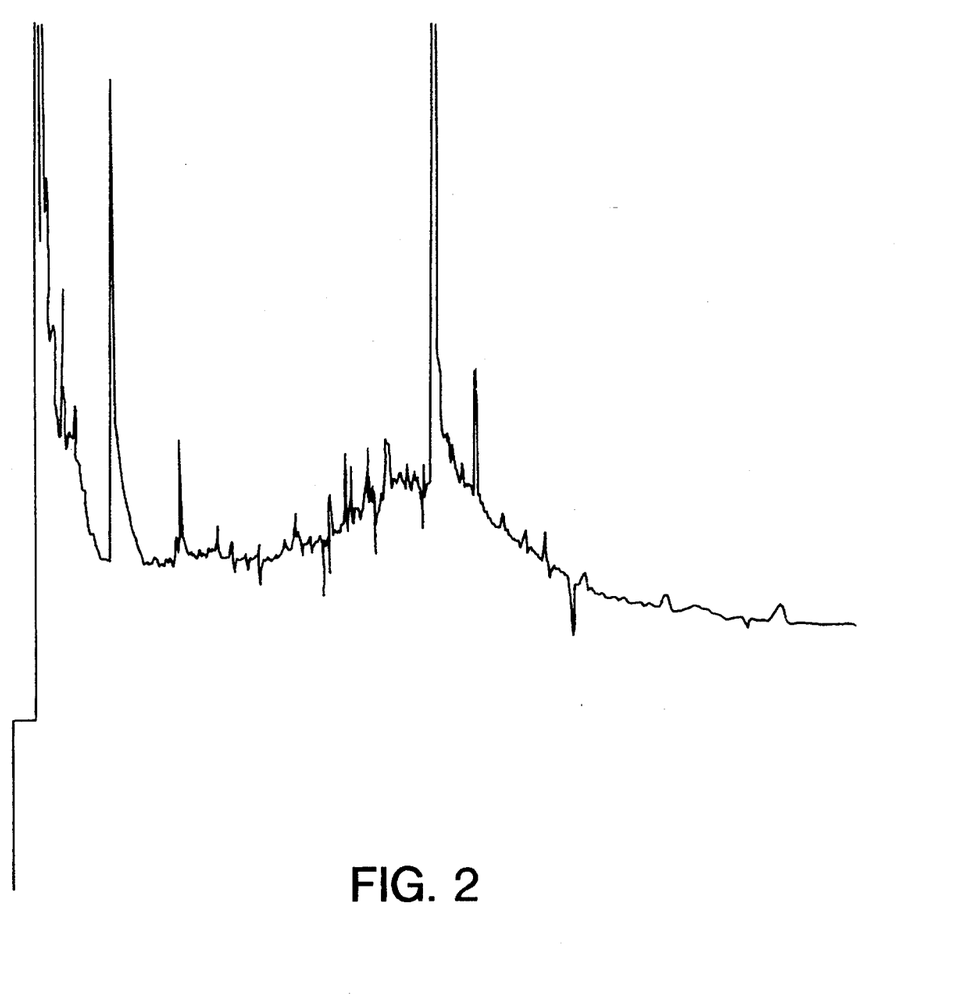
FIG. 2 is a reference chromatogram for SPME extraction of hexane solvent per se.

After removal of the SPME fiber from the hexane carrier matrix, the fiber was inserted into the injection port of a gas chromatograph equipped with an Electron Capture Detector, with thermal desorption conducted for trace pesticides and the resulting chromatogram, shown in FIG. 1, was obtained. This chromatogram is quite similar to a reference chromatogram as shown in FIG. 2 for a similar SPME extraction of hexane solvent alone. Thus, instead of the trace pesticides, the impurity peaks of hexane are shown as the major peaks in the chromatogram of FIG. 1.

The advantageous improvement of this invention is demonstrated in the following example of matrix exchange of the test sample solution of Comparative Example 1 followed by SPME extraction and detection.

EXAMPLE 2

Figure 3:
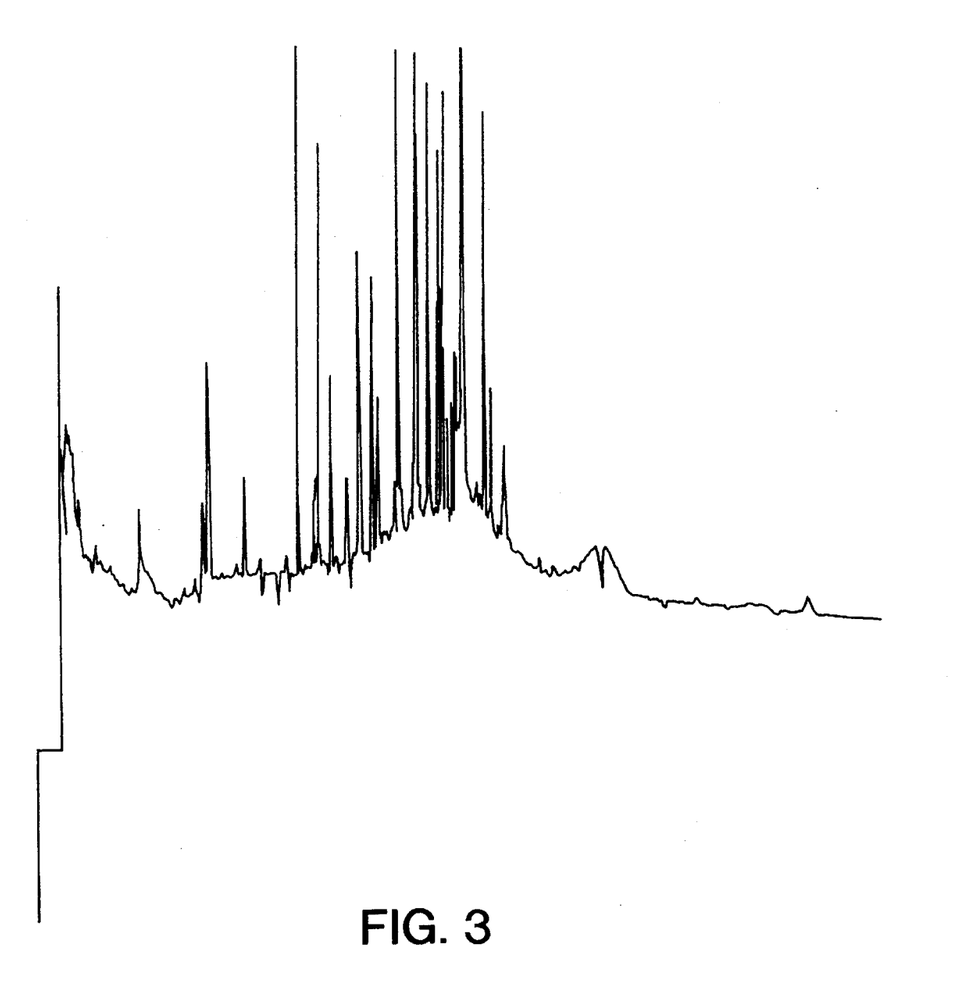
FIG. 3 is a chromatogram of a SPME extraction of trace organic pesticide analytes in an aqueous carrier matrix obtained according to the process improvement of this invention.

A test sample solution identical to Comparative Example 1 having 1 ppb of the 18 pesticides in 1 ml hexane solvent carrier matrix was provided and to this 1 ml of purified deionized water was then added to generate a two-phase mixture. The hexane solvent was then removed using a rotary evaporator under vacuum. Water bath at ambient temperature was used. This concentration process was stopped shortly after a homogeneous aqueous carrier based matrix solution was obtained as a detection sample. SPME was then conducted by inserting into the aqueous carrier based detection sample, for ten minutes, a SPME silica fiber coated with 7 μm poly(dimethylsiloxane). After removal of the SPME fiber from the aqueous carrier matrix detection sample, the fiber inserted into the injection port of a gas chromatograph with thermal desorption for trace pesticides and the resulting chromatogram, shown in FIG. 3, was obtained. The matrix exchange step has resulted in greatly enhanced, superior detection sensitivity such that pesticide peaks are readily detected.

Using the unique matrix exchange of this invention, organic solvent carrier matrices are exchanged to water or predominantly aqueous carrier matrices such that SPME extraction and detection of trace organic analytes in these resulting solutions give superior sensitivity enhancement. Therefore, the analyte enrichment power of common techniques such as liquid-liquid extraction can be successfully combined with SPME. The following example describes one of these combined procedures.

EXAMPLE 3

A first stage of analyte enrichment by liquid-liquid extraction is performed according to a modified EPA 608 procedure. Sodium chloride (100 grams) was dissolved in 1 liter of water sample containing the following listed fourteen semivolatile pesticides at 50 to 300 parts per trillion (ppt) levels to provide an environmental sample for analysis.

| | Chromatogram Peak No. | | Chromatogram Peak No. |
|---|---|---|---|
| Aldrin, 50 ppt | 6 | Dieldrin, 100 ppt | 10 |
| α-BHC, 50 ppt | 1 | Endosulfan I, 100 ppt | 8 |
| β-BHC, 50 ppt | 2 | | |
| γ-BHC, 50 ppt | 3 | 4,4'-DDT, 300 ppt | 14 |
| δ-BHC, 50 ppt | 4 | Endosulfan sulfate, 300 ppt | 13 |
| 4,4'-DDD, 300 ppt | 12 | Endrin, 100 ppt | 11 |
| 4,4'-DDE, 100 ppt | 9 | Heptachlor, 50 ppt | 5 |
| | | Heptachlor epoxide, 50 ppt | 7 |

Figure 4:
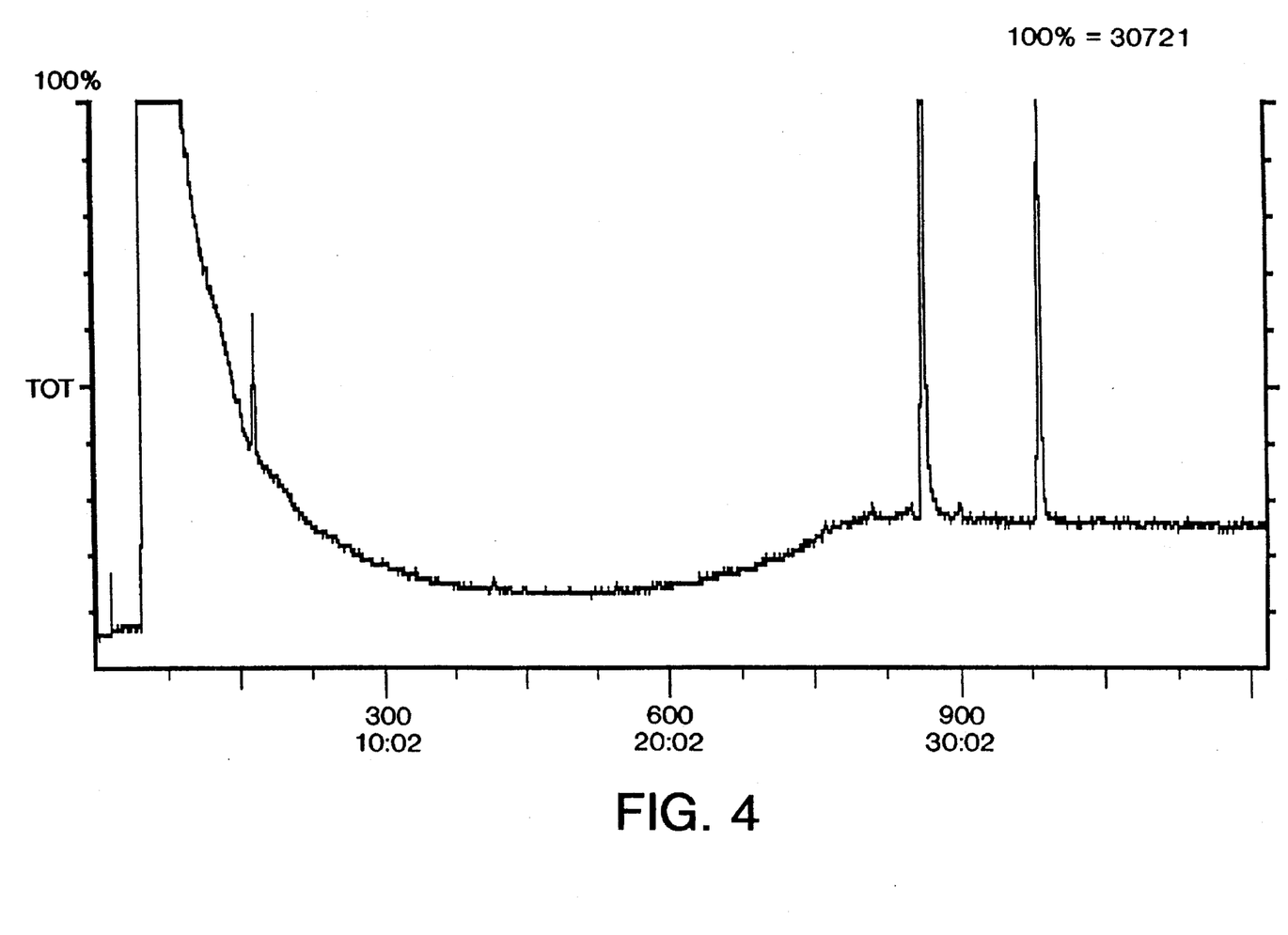
FIG. 4 is a chromatogram of a methylene chloride solvent based concentrate of 14 organic pesticide analytes.

This homogeneous solution was placed in a separatory funnel and extracted with 60 ml of methylene chloride. This methylene chloride extraction was repeated two additional times. The methylene chloride extracts were combined and concentrated to approximately 1 ml on a rotary evaporator under vacuum. This concentrated solution was transferred to a 10 ml flask for the matrix exchange. Gas chromatography/mass spectrometry analysis of this concentrate failed to detect any pesticides; only solvent and two phthalate contaminants were identified from the resulting chromatogram, shown in FIG. 4.

Figure 5:
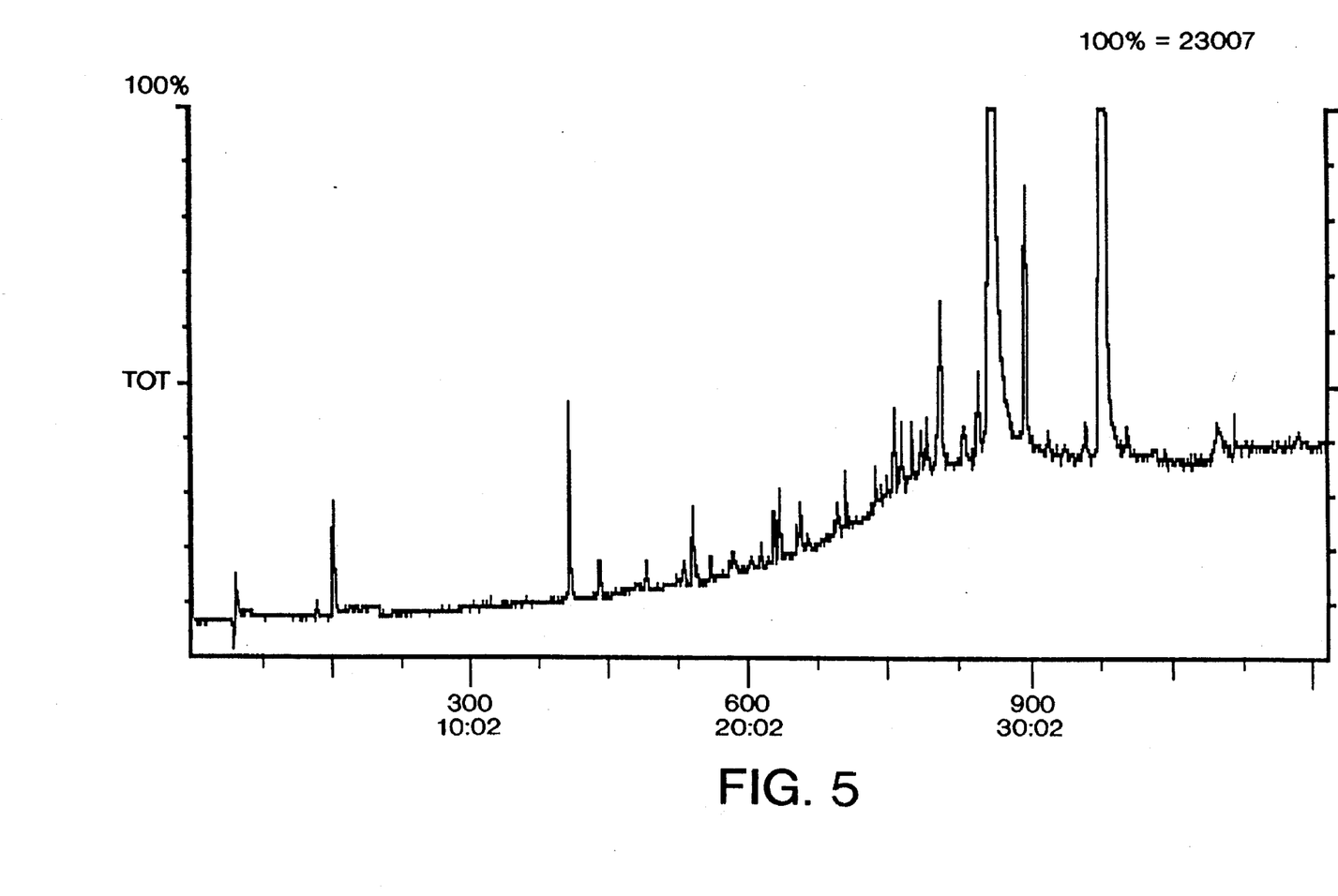
FIG. 5 is a chromatogram of a SPME extraction of trace organic pesticide analytes in an aqueous carrier matrix obtained according to the process improvement of this invention.
Figure 5A:
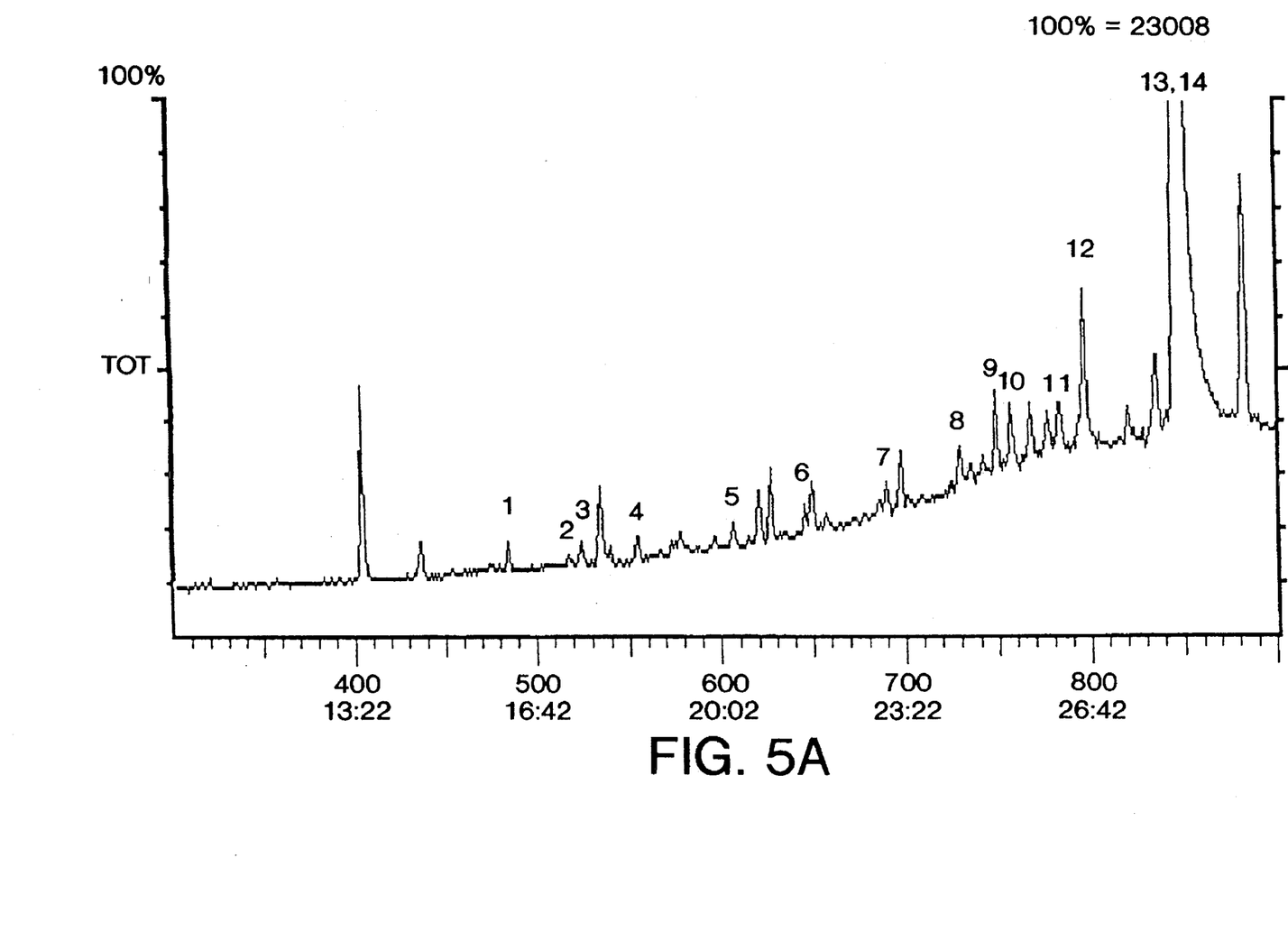
FIG. 5A is a detailed portion of the chromatogram of FIG. 5 identifying the pesticide peaks.

Next, the matrix exchange step of this invention is carried out. To the methylene chloride extracts was added 2 ml of 5% sodium chloride in water to produce a two-phase mixture. This two-phase mixture was concentrated to a homogeneous aqueous solution using a rotary evaporator under vacuum. Half of the resulting solution was transferred to a 1.5 ml vial. A SPME silica fiber, which is coated with 7 μm of poly(dimethylsiloxane), was inserted into the homogeneous aqueous solution for 15 minutes. After removal of the SPME fiber from the homogeneous aqueous solution the fiber was inserted into an injection port of a gas chromatography equipped with a mass spectrometer with thermal desorption conducted for the fourteen trace semivolatile organic pesticides and the resulting chromatogram, shown in FIG. 5 positively identified all fourteen pesticides with good signal-to-noise ratios. A detailed portion of the chromatogram in FIG. 5 is shown in FIG. 5A identifying the fourteen pesticide peaks. Endosulfan sulfate (No. 13) and 4,4' DDT (No. 14) coelute with an impurity peak.

Figure 6:
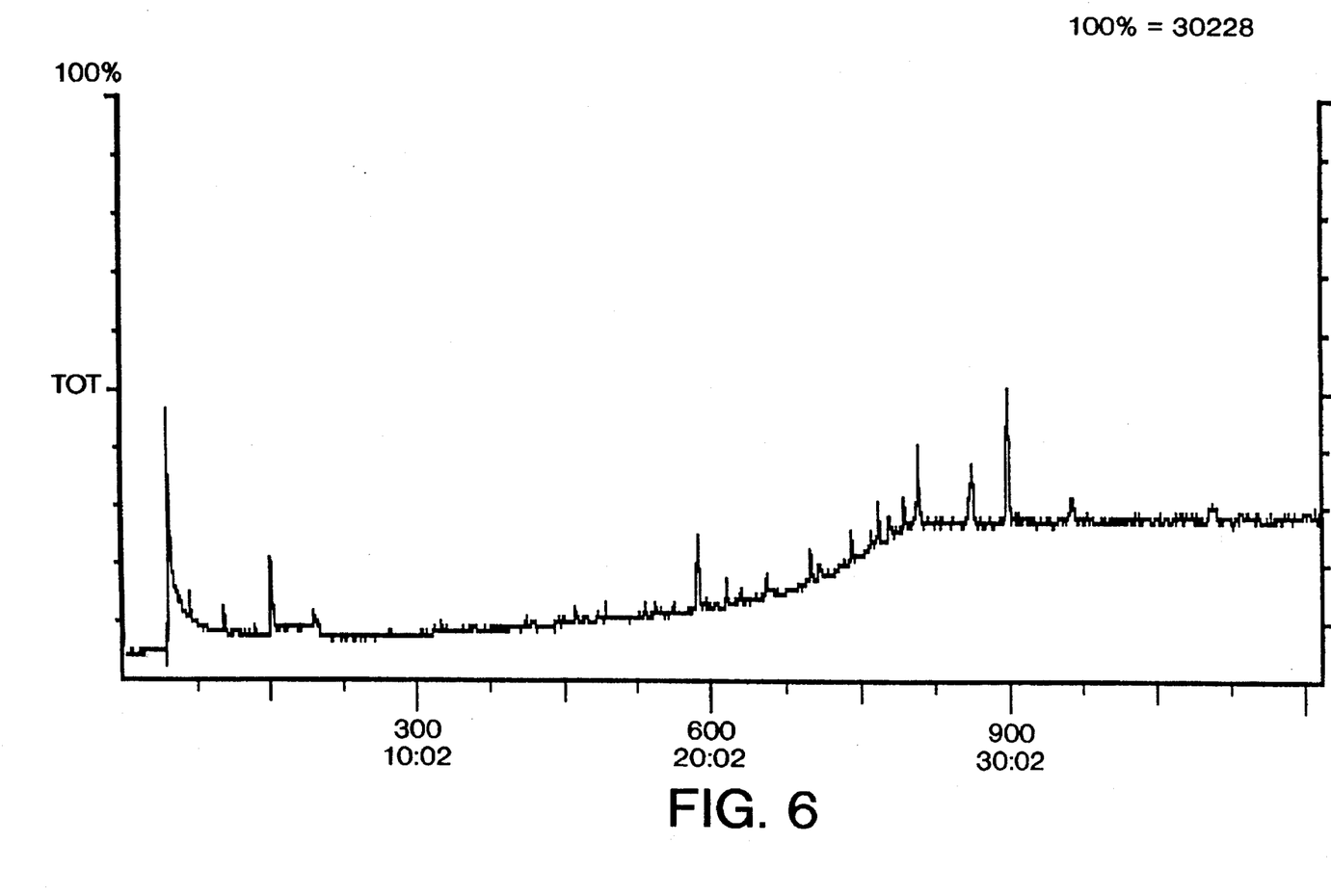
FIG. 6 is a chromatogram of a SPME extraction of trace organic pesticide analytes in an aqueous carrier matrix without the process improvement step of this invention.

For comparison, to show the enhanced detection sensitivity, direct SPME extraction of a 5% sodium chloride aqueous solution containing the aforementioned 14 semivolatile pesticides at 10 to 60 ppb levels and subsequent gas chromatography/mass spectrometry analysis was conducted. Analysis showed detection sensitivity of the fourteen pesticides as shown by the resulting chromatogram, FIG. 6. However, coupling of this SPME extraction procedure with other known sample enrichment procedure such as liquid-liquid extraction as shown in Example 3 demonstrates that improved detections sensitivity of more than 200-fold (FIG. 5) can be obtained compared to similar, direct SPME extraction of pesticides in aqueous matrices.

Figure 7:
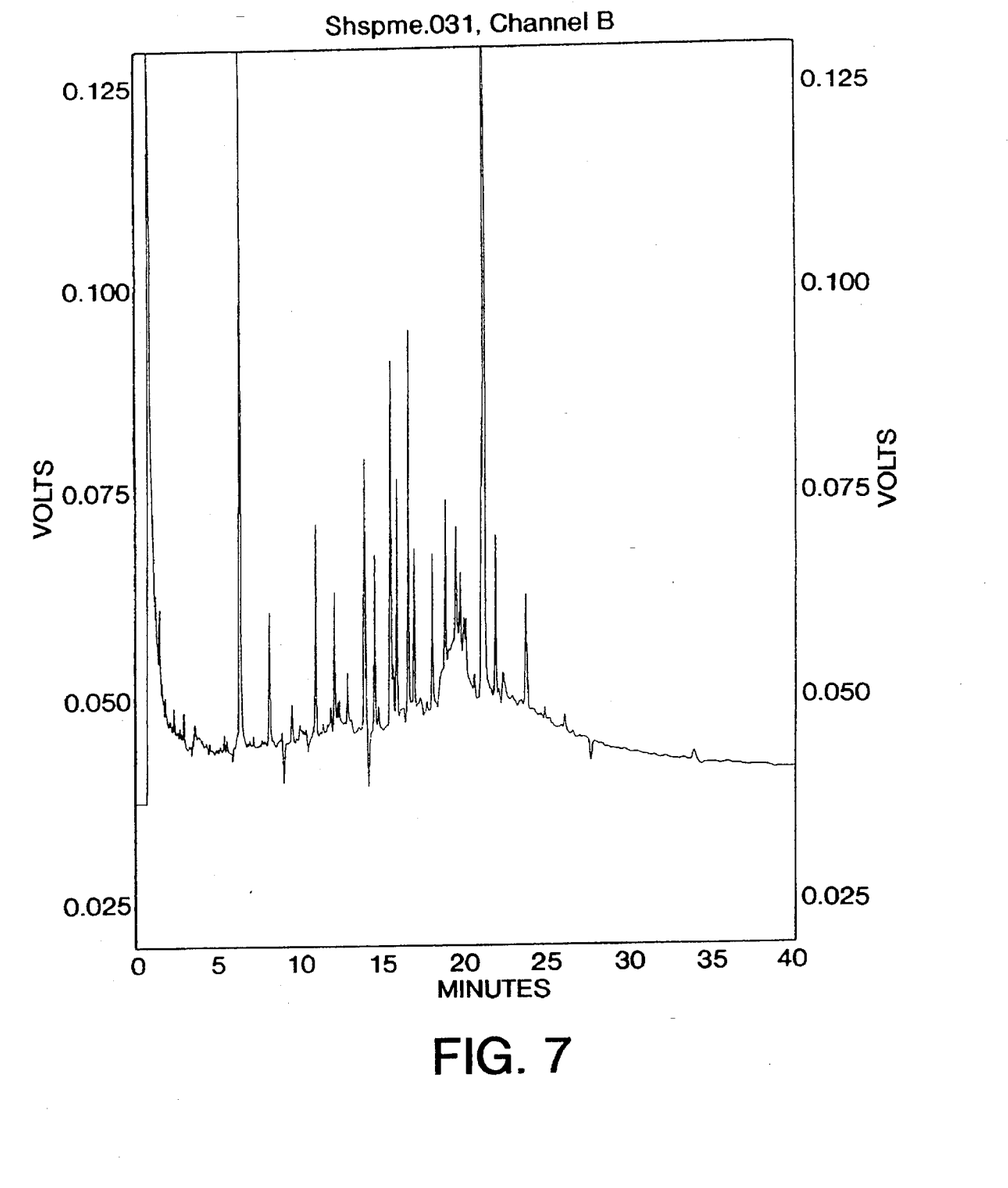
FIG. 7 is a chromatogram of a SPME extraction of trace (ppt and sub-ppt) organic pesticide analytes in an aqueous carrier matrix with the process improvement step of this invention.
Figure 8:
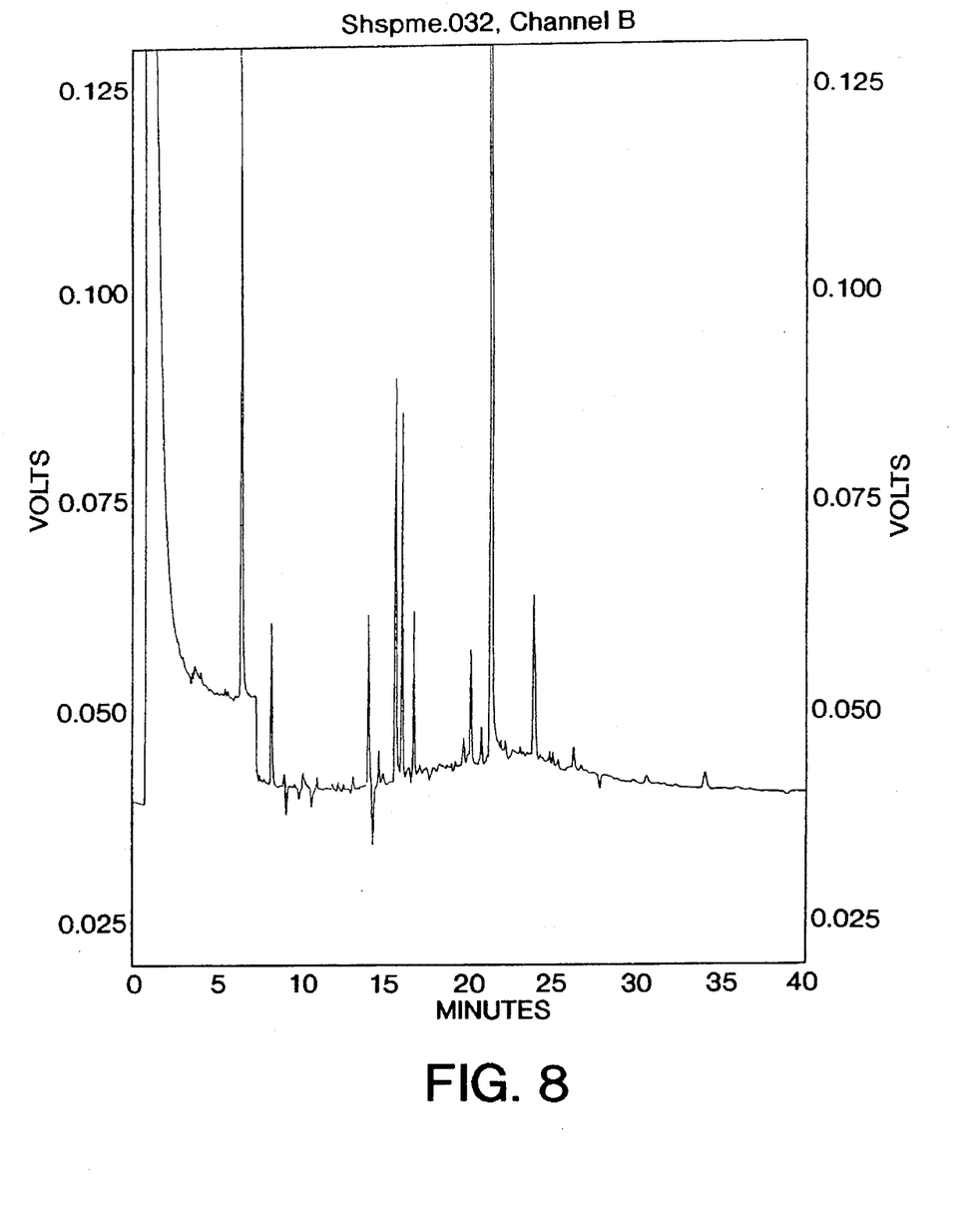
FIG. 8 is a reference chromatogram of the background matrix, reagents, solvents and SPME device employed in the SPME extraction resulting in the chromatogram in FIG. 7.

This powerful combination of SPME enables chlorinated pesticides at sub-parts per trillion levels using gas chromatograph with Electron Capture Detector. The chromatogram in FIG. 7 clearly demonstrates good detection of fourteen pesticides at 0.5 to 3 ppt. For comparison, the background chromatogram for matrix, reagents, solvents and the SPME device itself is shown in FIG. 8.

The superior, greatly enhanced detection sensitivity obtained from the combination of common organic solvent sample enrichment techniques, such as liquid-liquid techniques, with SPME enables reduced usage of sample, reagents and solvents yet still provides sufficient sensitivity in analysis which can result in significant material and time savings.

With the foregoing description of the invention, those skilled in the art will appreciate that modifications may be made to the invention without departing from the spirit thereof. Therefore, it is not intended that the scope of the invention be limited to the specific embodiments illustrated and described.

I claim:

1. In a method for detecting trace organic analytes suspected to be extracted into or dissolved in an organic solvent carrier matrix, which method comprises optionally concentrating said trace organic analytes in said organic solvent carrier matrix, and subsequently absorbing said trace organic analytes onto a fiber of a solid phase microextraction device and thereafter desorbing said trace organic analytes from said fiber into an analytical instrument for detection of one or more of said trace organic analytes, the improvement comprising:

prior to absorbing the trace organic analytes onto said fiber, conducting a matrix exchange by adding water to said organic solvent carrier matrix containing said trace organic analytes to produce a mixture and thereafter removing the organic solvent carrier matrix from said mixture to produce a detection sample of trace organic analytes in an aqueous carrier matrix for enhancing said adsorption of said trace organic analytes onto said fiber.

2. The method of claim 1 wherein the trace organic analytes are semivolatile organic analytes having a boiling point at least 25° C. above the boiling point of the organic solvent.

3. The method of claim 1 wherein the trace organic analytes are semivolatile organic analytes having a boiling point at least 50° C. above the boiling point of the organic solvent.

4. The method of claim 3 wherein the trace organic analytes are selected from the group consisting of pesticides, herbicides, polychlorinated biphenyl compounds and polynuclear aromatic hydrocarbon compounds.

5. The method of claim 1 wherein the extraction of trace organic analytes from the environmental sample is accomplished by liquid-liquid or liquid-solid extraction utilizing the organic solvent.

6. The method of claim 1 wherein the method enables detection of trace organic analytes at detection levels of parts per trillion.

7. The method of claim 1 wherein the method enables detection of trace organic analytes at detection levels of subparts per trillion.

8. The method of claim 1 wherein the organic solvent is removed from the mixture by evaporation of the organic solvent.

9. The method of claim 3 wherein the organic solvent is removed from the mixture by evaporation of the organic solvent.

10. The method of claim 5 wherein the organic solvent is removed from the mixture by evaporation of the organic solvent.

11. A method for enhanced detection of trace amounts of organic analytes in an environmental sample, said method comprising:

(1) providing an environmental sample suspected of containing trace amounts of organic analytes, (2) if said environmental sample does not already have an organic solvent carrier matrix, organic solvent-extracting any such trace amounts of organic analytes from said environmental sample into an organic solvent carrier matrix in which said trace amounts of organic analytes are soluble, (3) optionally concentrating said trace amounts of organic analytes in said organic solvent carrier matrix by removal of a portion of said organic solvent, (4) thereafter, exchanging said organic solvent carrier matrix of said test sample by the addition thereto of water to form a mixture and removing said organic solvent carrier matrix therefrom producing a detection sample comprising an aqueous carrier matrix containing said trace amounts of organic analytes, and thereafter performing solid phase microextraction on said detection sample by (5) placing a fiber of a solid phase microextraction device in contact with said aqueous carrier matrix or a confined headspace above said aqueous carrier matrix for a sufficient period of time for extraction of the trace organic analytes from the aqueous carrier matrix and onto the fiber to occur, (6) subsequently removing said fiber from said aqueous carrier matrix or confined headspace and desorbing the organic analytes from the fiber into an analytical instrument for detection of one or more of said trace organic analytes, and (7) detecting one or more of said organic analytes in said analytical instrument.

12. The method of claim 11 wherein the trace organic analytes are semivolatile organic analytes having a boiling point at least 25° C. above the boiling point of the organic solvent.

13. The method of claim 11 wherein the trace organic analytes are semivolatile organic analytes having a boiling point at least 50° C. above the boiling point of the organic solvent.

14. The method of claim 13 wherein the trace organic analytes are selected from the group consisting of chlorinated pesticide compounds, herbicide compounds, polychlorinated biphenyl compounds and polynuclear aromatic hydrocarbon compounds.

15. The method of claim 11 wherein the extraction of trace organic analytes from the environmental sample is accomplished by liquid-liquid or liquid-solid extraction utilizing the organic solvent.

16. The method of claim 11 wherein the method enables detection of trace organic analytes at detection levels of parts per trillion.

17. The method of claim 11 wherein the method enables detection of trace organic analytes at detection levels of subparts per trillion.

18. The method of claim 11 wherein the organic solvent is removed from the mixture by evaporation of the organic solvent.

19. The method of claim 13 wherein the organic solvent is removed from the mixture by evaporation of the organic solvent.

20. The method of claim 15 wherein the organic solvent is removed from the mixture by evaporation of the organic solvent.

* * * * *